(12) United States Patent
Watkins et al.

(10) Patent No.: US 7,608,465 B2
(45) Date of Patent: *Oct. 27, 2009

(54) MULTI-ANALYTE DIAGNOSTIC TEST FOR THYROID DISORDERS

(75) Inventors: Michael I. Watkins, Vacaville, CA (US); Suknan S. Chang, Oakland, CA (US); Renato B. Del Rosario, Benicia, CA (US); Patricia A. Miranda, Novato, CA (US); Timothy D. Knight, Benicia, CA (US); Richard B. Edwards, Cold Spring, NY (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/243,145

(22) Filed: Sep. 13, 2002

(65) Prior Publication Data

US 2003/0054571 A1    Mar. 20, 2003

Related U.S. Application Data

(60) Division of application No. 09/548,883, filed on Apr. 13, 2000, now Pat. No. 7,271,009, which is a continuation-in-part of application No. 09/302,920, filed on Apr. 30, 1999, now Pat. No. 6,280,618.

(51) Int. Cl.
G01N 33/53 (2006.01)
(52) U.S. Cl. .................. 436/500; 435/7.1; 435/7.94; 435/176; 435/287.2; 435/973; 436/518; 436/526; 436/172; 422/73; 422/82.08; 422/101

(58) Field of Classification Search .................. 435/7.1, 435/7.92, 7.93, 7.94, 7.95, 287.2, 973, 174, 435/176, 182; 436/500, 501, 507, 546, 513, 436/172, 518, 823, 523–534; 422/73, 82.05, 422/82.08, 101
See application file for complete search history.

(56) References Cited

U.S. PATENT DOCUMENTS 4,032,626 A    6/1977    Ward (Continued)

FOREIGN PATENT DOCUMENTS

WO    WO 95/02824 A1    1/1995

OTHER PUBLICATIONS

Yamashiro et al., Augmentation of TSAb-stimulated cAMP response by PEG, PVA, and dextran; highly sensitive porcine thyroi cell TSAb assay. Thyroid : official journal of the American Thyroid Association, (Mar. 1999) 9 (3) 263-71. (Abstract).*

(Continued)

Primary Examiner—Gailene R Gabel
(74) Attorney, Agent, or Firm—Townsend and Townsend and Crew LLP.; M. Henry Heines

(57) ABSTRACT

Immunological assays for several biological markers for thyroid disorders in a biological sample are performed in a single test with a combination of sandwich-type, sequential competitive, and serological assays by the use of particles classified into groups that are distinguishable by flow cytometry, one group for the assay of each marker. Each group of particles is coated with a different immunological binding member, and coating densities, co-coating materials, and special buffer solutions are used to adjust for differences in the sensitivities and dynamic ranges of each of the markers in the typical sample.

11 Claims, 10 Drawing Sheets

U.S. PATENT DOCUMENTS

| | | | |
|---|---|---|---|
| 4,332,784 | A | 6/1982 | Smith et al. |
| 4,824,777 | A | 4/1989 | Chang et al. |
| 5,071,773 | A | 12/1991 | Evans et al. |
| 5,346,670 | A | 9/1994 | Renzoni et al. |
| 5,639,670 | A | 6/1997 | Bergmann et al. |
| 5,723,346 | A | 3/1998 | Frengen |
| 5,795,789 | A | 8/1998 | Dietzen |
| 5,858,648 | A * | 1/1999 | Steel et al. ............... 435/5 |
| 5,972,721 | A * | 10/1999 | Bruno et al. ............ 436/526 |
| 5,981,180 | A * | 11/1999 | Chandler et al. ............ 435/6 |
| 6,280,618 | B2 * | 8/2001 | Watkins et al. ............ 210/222 |
| 7,271,009 | B1 * | 9/2007 | Watkins et al. ............ 436/526 |

OTHER PUBLICATIONS

Ochi et al., Clinical usefulness of TSAb assay with high polyethylene glycol concentrations. Hormone research, (1999) 51 (3) 142-9 (Abstract).*

Block, P. Jr. "Synthesis of 3-iodo-L-thyronine and its iodinated derivatives," *J. Med. Chem.* 1976, pp. 1067-1069, vol. 19, No. 8.

Fert, V. et al., "A new flow cytometry-based multi-assay system: 3. Application to hormone immunoassays," Cytometry, 1998, pp. 132-133, vol. Suppl. 9.

Frieden, E. et al. "The thyroxine-like activity of compounds structurally related to thyroxine," *J. Biol. Chem.* 1948, pp. 155-163, vol. 176.

Fulwyler and McHugh "Flow microsphere immunoassay for the quantitative and simultaneous detection of multiple soluble analytes," *Meth. Cell Biol.* 1990, pp. 613-629, vol. 33, Chapter 51.

Gosling "A decade of development in immunoassay methodology," *Clin. Chem.* 1990, pp. 1408-1426, vol. 36, No. 4.

Jaume, J. et al., "Thyrotropin receptor autoantibodies in serum are present at much lower levels than thyroid peroxidase autoantibodies: Analysis by flow cytometry," Journal of Clinical Endocrinology & Metabolism, 1997, pp. 500-507, vol. 82(2).

Kendler, D. L. et al., "Detection of autoantibodies to recombinant human thyroid peroxidase by sensitive enzyme immunoassay," Clinical Endocrinology, Dec. 1990, pp. 751-760, vol. 33(6), Blackwell Scientific Publications, Oxford, Great Britain.

McHugh "Flow cytometry and the application of microsphere-based fluorescene immunoassay," *Immunochemica* Jan. 1991, pp. 1-6, vol. 5, No. 1.

Zbinden, G., "Evaluation of thyroid gland activity by hormone assays and flow cytometry in rats," Experimental Cell Biology, 1988, pp. 196-200, vol. 56(4).

Ochi et al., Hormone Research 51: 142-149 (1999).

Yamashiro et al., Thyroid 3:263-271 (1999).

Rubbi, Carlos P. et al.; "Evidence of surface antigen detachment during incubation of cells with immunomagnetic beads"; 1993, *Journal of Immunological Methods*, vol. 166, pp. 233-241.

Sun, Liping et al.; "Continuous, Flow-Through Immunomagnetic Cell Sorting in a Quadrupole Field"; 1998, *Cytometry*, vol. 33, pp. 469-475.

Vlieger, A.M. et al.; "Quantitation of Polymerase Chain Reaction Products by Hybridization-Based Assays with Fluorescent, Colorimetric, or Chemiluminescent Detection"; 1992, *Journal of Analytical Biochemistry*, vol. 205, pp. 1-7.

* cited by examiner

TPO Standard Curve

FT3 Standard Curve

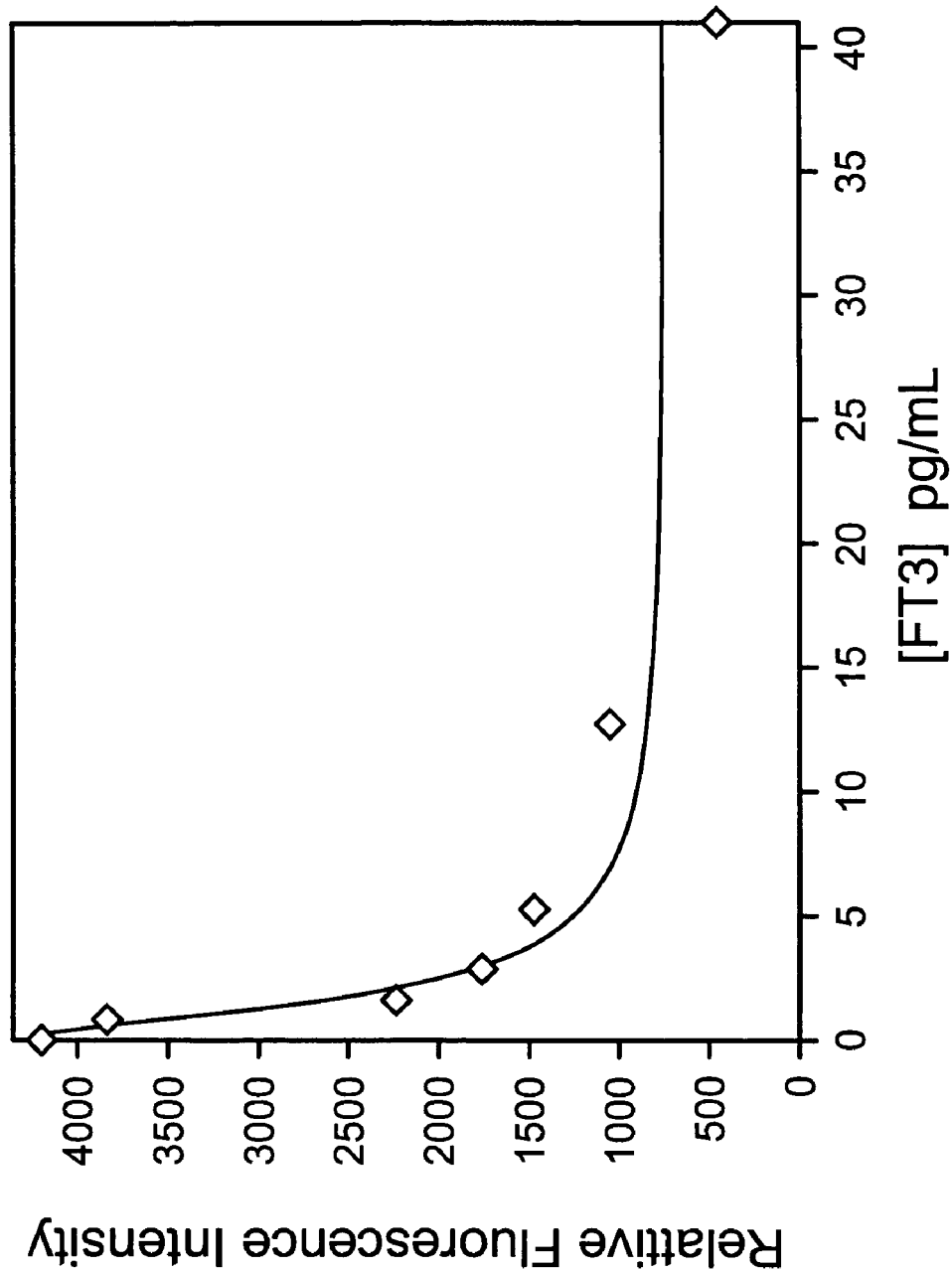

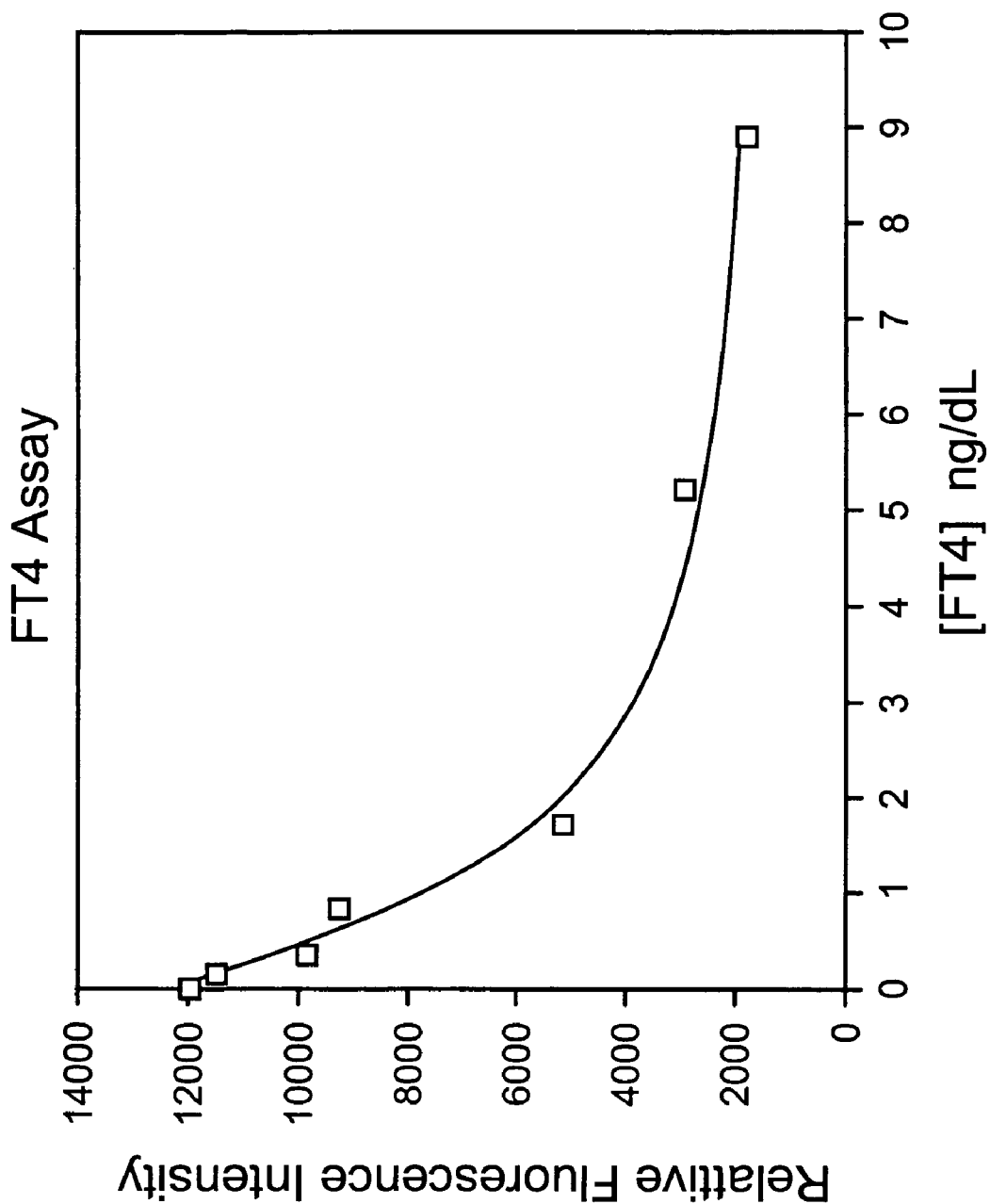

MULTI-ANALYTE DIAGNOSTIC TEST FOR THYROID DISORDERS

CROSS-REFERENCE TO RELATED APPLICATIONS

This application is a divisional application of application Ser. No. 09/548,883 filed Apr. 13, 2000, now U.S. Pat. No. 7,271,009 which is a continuation-in-part of application Ser. No. 09/302,920 filed Apr. 30, 1999 (now U.S. Pat. No. 6,280,618) of Michael I. Watkins and Richard B. Edwards.

BACKGROUND OF THE INVENTION

Thyroid disorders are among the most common endocrinological diseases. Hypothyroidism, in which the thyroid glands produce too little hormone, can reduce the metabolic rate to as low as half the normal rate, while hyperthyroidism, in which an excess of thyroid hormone is produced, can double it. Between 8 and 9 million Americans suffer from hypothyroidism and its associated diseases, which include Hashimoto's thyroiditis (chronic lymphocytic thyroiditis) which affects 1 out of 5 women over the age of 75, nontoxic goiter (iodine deficiencies), neonatal goiter (cretinism), and Riedel's thyroiditis. Approximately 350,000 Americans suffer from hyperthyroidism in the form of Grave's disease (toxic goiters or thyrotoxicosis), toxic nodular goiter, neonatal hyperthyroidism, and iatrogenic hyperthyroidism.

Methods for the detection of thyroid disorders utilize several species in the bloodstream as biological markers whose levels are measured as an indication of the presence and type of disorder. Triiuodothyronine (T3) and thyroxine (T4) are two of the markers. In conditions of hypothyroidism, the levels of these markers, which are normally within the ranges of 1.1-2.9 nmol/L and 64-142 nmol/L in serum, respectively, are low, while in conditions of hyperthyroidism they are elevated. Another marker, thyroid stimulating hormone (TSH), varies in the opposite direction by being elevated in conditions of hypothyroidism and depressed in conditions of hyperthyroidism, both relative to a normal serum level of 0.5-5 mIU/L. In certain conditions, notably Hashimoto's thyroiditis, anti-thyroglobulin (anti-Tg) antibodies and anti-thyroid peroxidase (anti-TPO) antibodies (the latter also referred to as antimicrosomal antibodies), which are additional markers, are also elevated, although an anti-TPO determination without an anti-Tg determination is often considered adequate. Other tests include measurements of the basal metabolic rate and closed percutaneous biopsies of the thyroid.

To diagnose a thyroid disorder by serum analyses, the physician thus needs to detect the levels of either four or five markers. Using an individual procedure for each marker can be an expensive undertaking in terms of materials, equipment, and labor, and the risk of error is proportional to the number of procedures performed. By contrast, if the physician can detect all of the markers in a single test, the cost would be less, the probability of error would be significantly decreased, and the risk of the need for a repeat test (and the awkwardness of requesting an additional blood sample from the patient) would be lessened. In addition, the time involved in diagnosis, treatment, and recovery may be substantially reduced.

Unfortunately, the development of a unified or simultaneous test procedure has thus far been discouraged by the technology required to perform multianalyte analyses and by differences among the properties of the particular markers. Some but not all of the markers are antibodies, some are small molecules and others large, and some are present in lower concentrations than others and therefore require assays of greater sensitivity. While each can be detected by an immunoassay of some kind, the chemistries of the immunoassay differ from one analyte to the next, and different reagents are added at different times. It is indeed a challenge to accommodate these differences and produce an assay that can provide individual values for each of the markers and yet be performed in a single reaction mixture.

SUMMARY OF THE INVENTION

It has now been discovered that a single-reaction-mixture multiplexed assay to detect the individual levels of either all five markers or all five minus anti-Tg can be performed by using a single mixture of particles that differ from each other according to a plurality of groups, each group having a distinctive property that permits it to be distinguished from the others by flow cytometry and each group bearing a surface coating of an immunological binding member having selective affinity for one of the analytes to be detected. One group of particles (and in some cases, two groups to achieve a wider range of detection) is thus coated with anti-TSH, a second group is coated with antibodies to T3, a third group is coated with antibodies to T4, and a fourth group is coated with either TPO or anti-human IgG. If the sample is to be assayed for Tg, the fourth group will be coated TPO and a fifth group will be coated with Tg. Each group will thus have both a distinctive coating for purposes of the individual analyte that it is directed to and an additional distinctive characteristic that will enable it to be distinguishable by flow cytometry.

The entire mixture of particles is suspended in the sample and the suspension is incubated for an appropriate period of time to permit the immunological reaction to occur. The particles are then recovered and resuspended in a solution of labeled binding members which includes labeled anti-TSH, a labeled analog of T3 and T4 chosen such that the antibody on either the FT3 or FT4 particles has lower affinity toward the analog than toward T3 or T4, and either labeled anti-human IgG or labeled TPO. The last binding member will be labeled anti-human IgG if the fourth group of particles is coated with TPO and also if the fifth group mentioned above is present, and will be labeled TPO if the fourth group of particles is coated with anti-human IgG.

After sufficient time has passed for the immunological reaction at the surfaces of the resuspended particles to occur, the particles are recovered from the second suspension and the amount of particle-bound label is detected while the particles are distinguished by flow cytometry. Individual values are thus obtained for the amounts of TSH, T3, T4, and anti-TPO, and where desired, anti-Tg, in the sample, all obtained from a common assay mixture in which all reagent additions, incubations, particle recovery steps, washing steps, and detection steps for each analyte are performed. The assay thus combines a sandwich assay for TSH with sequential competitive assays for T3 and T4 and a serological assay(s) for TPO (and Tg, where included).

The assays of this invention thus combine a sandwich-type immunoassay for TSH with sequential competitive immunoassays for T3 and T4 and serological assays for anti-TPO and anti-Tg. The combination of sandwich and sequential competitive assays permits the simultaneous detection of a molecule sufficiently large to permit binding to two antibodies (TSH) and molecules too small to permit such two-antibody binding (T3 and T4). The combination of sandwich and sequential competitive assays with serological assays permits the simultaneous detection of antigen analytes and antibody analytes. Furthermore, since levels of the various analytes differ considerably with some requiring assays of greater sensitivity than others, accommodations are made by lowering the signals of some of the assays, notably the anti-TPO and anti-Tg assays. This is achieved by the use of a diluting agent as an additional coating member on the particles of the respective particle groups, thereby lowering the reaction rate of the immunological reaction. In preferred embodiments, an additional accommodation is made by the addition of polyethylene glycol to the suspension in which the labeled binding members are added, to increase the reaction rate and hence the sensitivity of the TSH portion of the assay. In further preferred embodiments, two mutually distinguishable particle groups are used for the measurement of TSH, each particle group optimized for a different portion of the analytical range.

In a further aspect of this invention, individual levels of two markers, TSH and T4, are detected in a single sample by using a single mixture of particles divided into groups differing from each other in the manner described above. This aspect of the invention combines a sandwich-type assay for TSH with a sequential competitive assay for T4.

Additional objects, features, and advantages of the invention will become apparent from the description that follows.

BRIEF DESCRIPTION OF THE DRAWINGS

FIG. 7 is a standard curve for FT3 generated from a multiplexed assay for FT4 and FT3 in accordance with this invention.

FIG. 8 is a standard curve for FT4 generated from a multiplexed assay for FT4 and FT3 in accordance with this invention.

DETAILED DESCRIPTION OF THE INVENTION AND SPECIFIC EMBODIMENTS

Figure 1A:
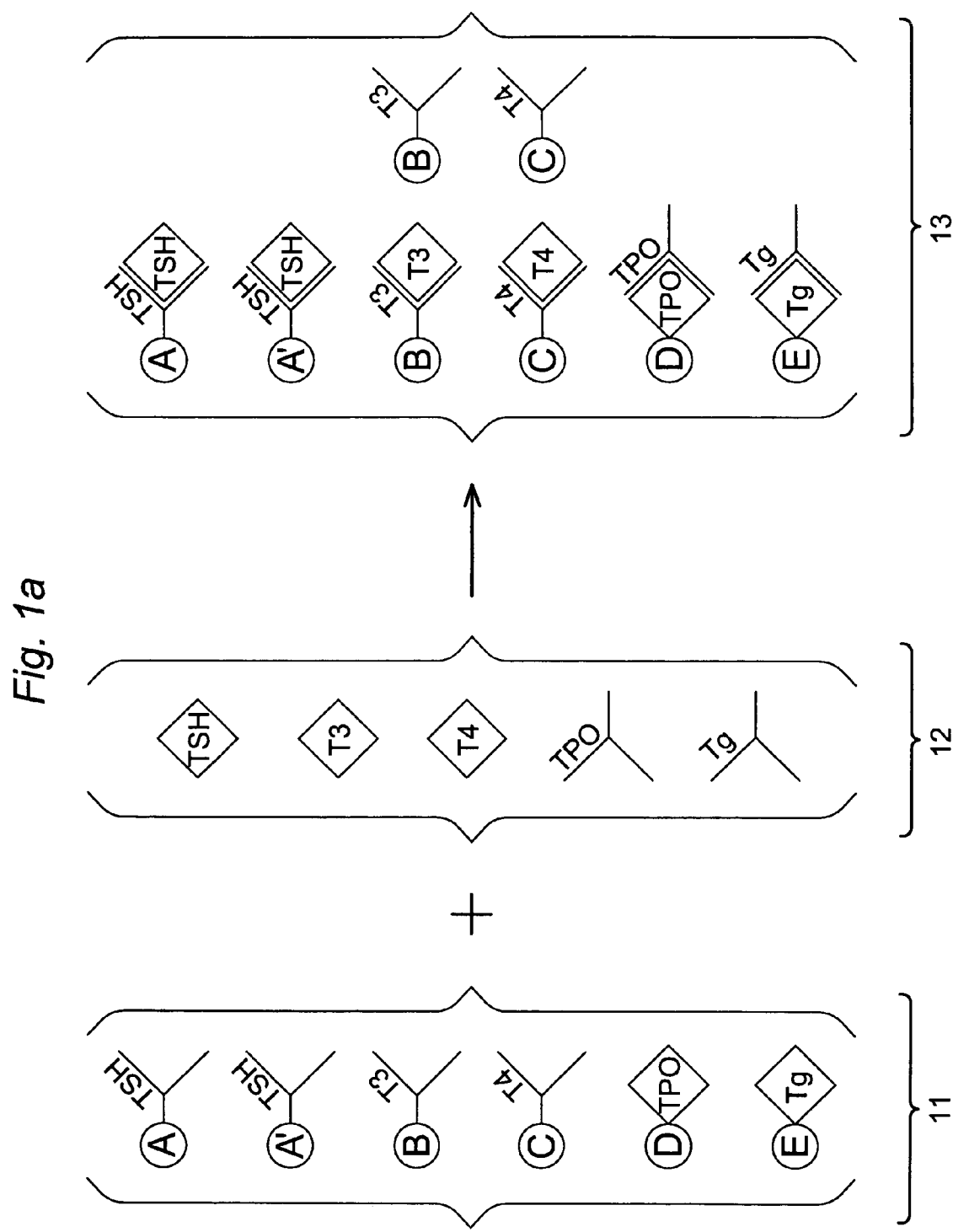
FIGS. 1a and 1b together form a diagram of one assay in accordance with this invention, showing the various particles, binding members, and types of binding reactions that take place.
Figure 1B:
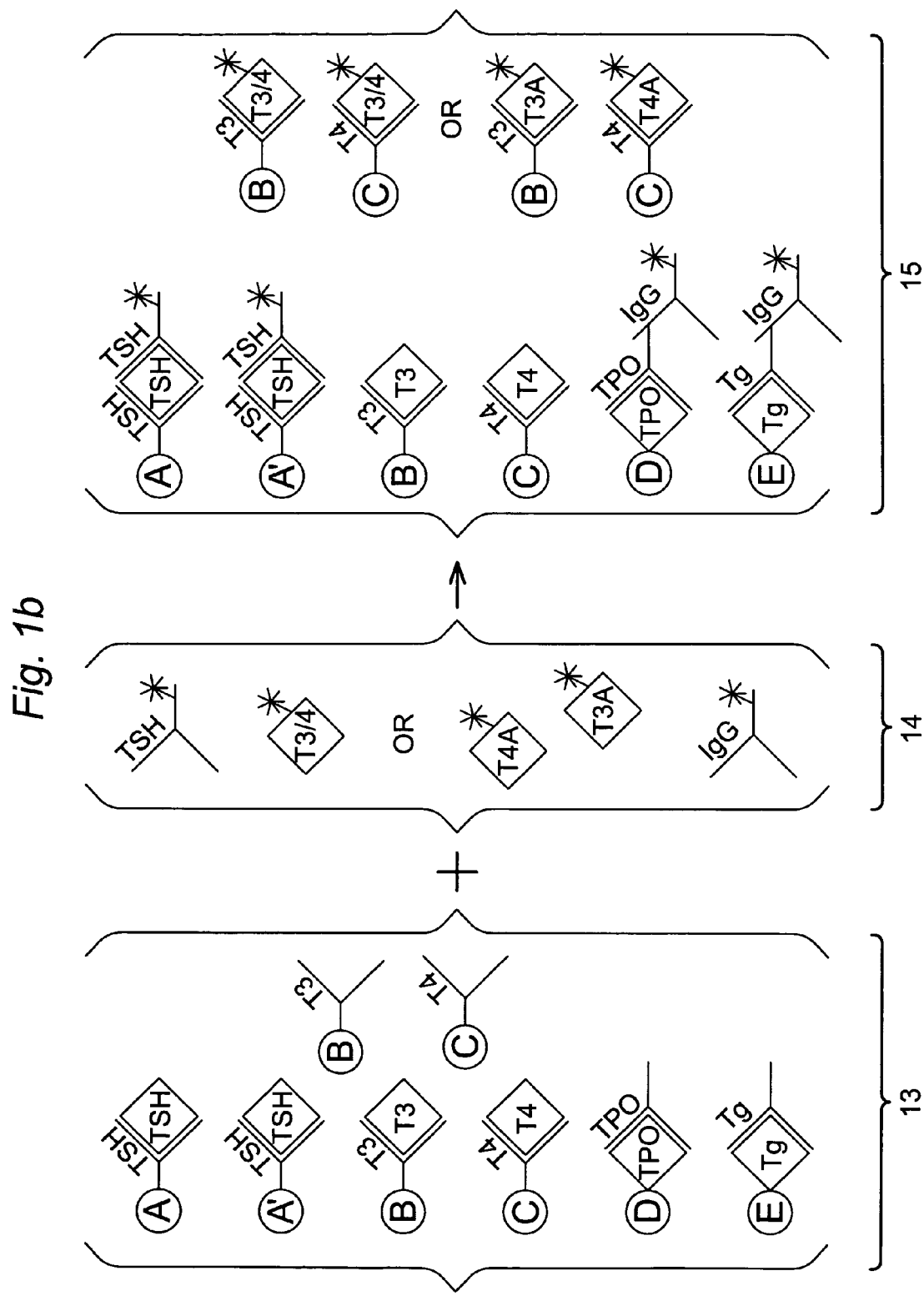

A pictorial representation of an assay in accordance with this invention for all five markers appears in FIGS. 1a and 1b. The mixture of coated particles 11 contains six distinct groups of particles and is represented by a column of circles with the letters A (and A') through E inside the circles and with either antibodies or antigens attached. Each letter designates a distinct group of particles distinguishable from the others by flow cytometry (A and A' being distinguishable from each other as well), and the structures attached to the circles represent the coatings on the particles. Particles A, A', B, and C have surfaces coated with anti-TSH (both A and A'), anti-T3 (B), and anti-T4 (C) antibodies, each antibody represented by a sideways "Y," structure with the specificity of each antibody indicated on one Fab chain of the structure. Particles D and E are coated with TPO and Tg, respectively, each represented by a diamond surrounding the abbreviation of the particular antigen. The "A" particles differ in sensitivity from the "A'" particles due to differences in TSH coating density and particle size.

The sample 12 to be assayed is represented by the column to the right of the particles column 11. Included in the sample 12 are the analytes TSH, T3, T4, anti-TPO, and anti-Tg. The TSH, T3, and T4 are represented by the three diamond structures at the top, respectively, and anti-TPO and anti-Tg are represented by the two "Y" structures at the bottom, respectively.

After incubation, particle recovery, and washing, the following mixture of particles 13 results:

"A" and "A'" particles with TSH from the sample bound to the particles through the anti-TSH coating on the particles. Some sites on the "A" and "A'" particles remain that do not have TSH bound to them, but these are not shown since they do not take part in the remainder of the assay, even though they are present on the particles.

"B" particles with T3 from the sample bound to the particles through the anti-T3 coating on the particles. Some sites on the "B" particles remain that do not have T3 bound to them. These sites are shown as separate particles in the diagram and undergo binding reactions in succeeding steps of the assay, as described below.

"C" particles with T4 from the sample bound to the particles through the anti-T4 coating on the particles. Some sites on the "C" particles remain that do not have T4 bound to them. These sites are likewise shown as separate particles in the diagram and undergo binding reactions in succeeding steps of the assay, as described below.

"D" particles with anti-TPO from the sample bound to the particles through the TPO antigen coating on the particles. Here again, some sites on the "D" particles will remain that do not have TPO antibodies bound to them, but they do not take part in the remainder of the assay, and are therefore not shown.

"E" particles with anti-Tg from the sample bound to the particles through the Tg antigen coating on the particles. Here as well, less than all of the available sites on the "E" particles become bound to Tg antibodies, but these free sites remain unbound for in the remainder of the assay and are therefore not shown.

This particle mixture is resuspended with a mixture of labeled binding members 14. This mixture includes (i) labeled anti-TSH, (ii) either a labeled analog of T3 and T4 (represented by the diamond containing the indicium "T3/4") which binds to both anti-T3 and anti-T4 or individual labeled analogs of T3 and T4 (represented by the indicia "T3A" and "T4A", respectively) which bind preferentially to anti-T3 and anti-T4, respectively, and (iii) labeled anti-human IgG. The label on each of these labeled binding members is represented by an asterisk. The labeled analog represented by "T3/4" is one toward which both anti-T3 and anti-T4 have less affinity than they have toward T3 or T4 themselves. The analog therefore binds only to those antibodies that have not already become bound to T3 and T4. The same is true of the individual labeled analogs T3A and T4A.

After incubation, particle recovery, and washing, the result is a particle mixture 15 that includes:

"A" and "A'" particles representing the result of sandwich assay, the analyte TSH positioned between the anti-TSH coating on the particle surface and the labeled anti-TSH, the label thus giving a direct indication of the amount of TSH in the sample.

A mixture of "B" particles, labeled and unlabeled, that is the result of a sequential competitive assay, the labeled "B" particles (the two alternatives are shown, depending on which labeled analog was used) representing those sites to which the analyte T3 did not become bound, thereby giving an inverse indication of the amount of T3 in the sample.

A mixture of "C" particles, labeled and unlabeled, that is the result of a sequential competitive assay, the labeled "C" particles (the two alternatives are shown, depending on which labeled analog was used) representing those sites to which the analyte T4 did not become bound, thereby giving an inverse indication of the amount of T4 in the sample.

"D'" particles representing the result of an indirect or "antigen-capture" serological assay, the analyte anti-TPO positioned between the TPO coating on the particle surface and the labeled anti-human IgG, the label thus giving a direct indication of the amount of anti-TPO in the sample.

"E" particles representing the result of an indirect or "antigen-capture" serological assay, the analyte anti-Tg positioned between the Tg coating on the particle surface and the labeled anti-human IgG, the label thus giving a direct indication of the amount of anti-Tg in the sample.

Figure 2A:
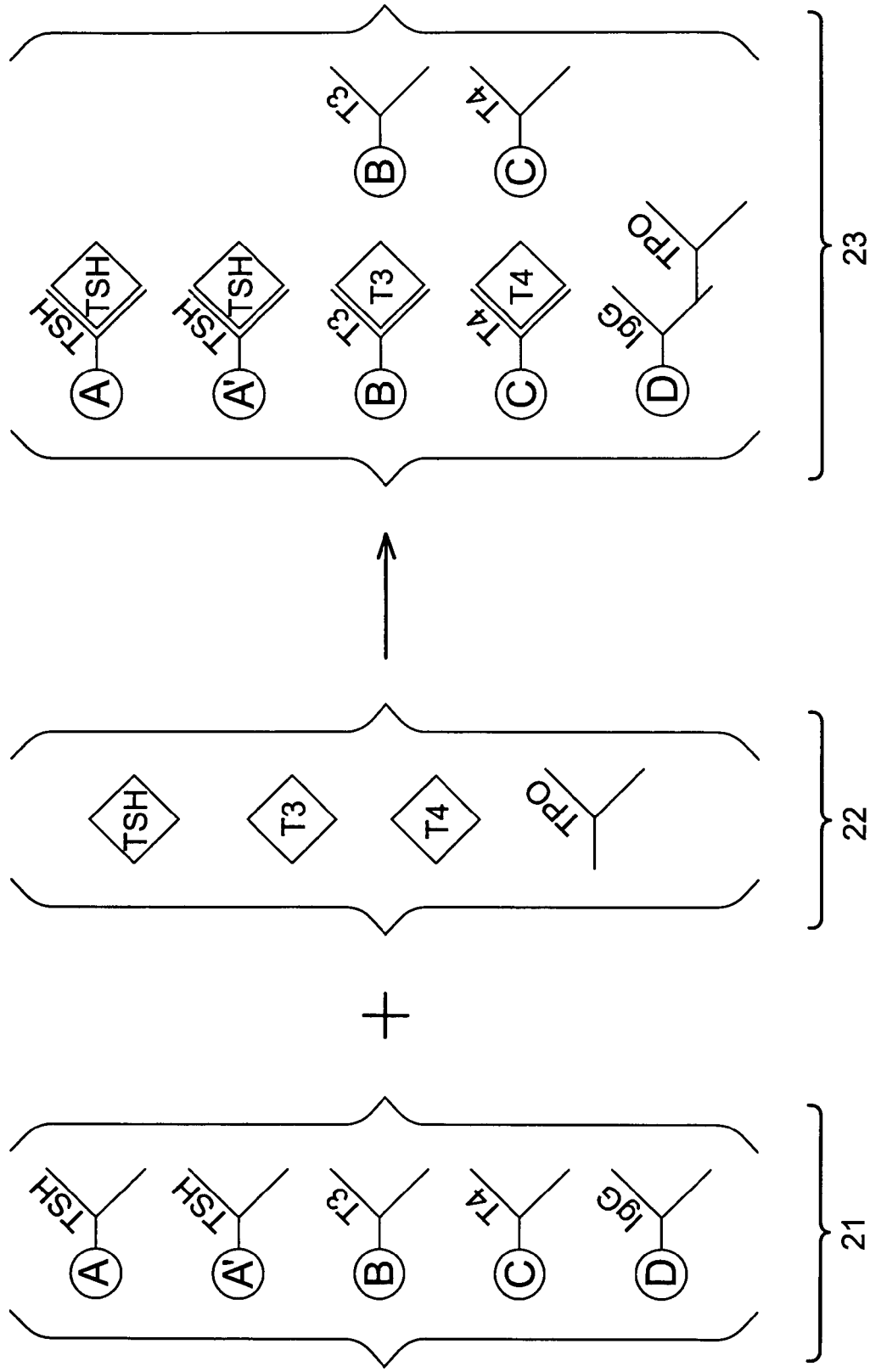
FIGS. 2a and 2b together form a diagram of another assay in accordance with this invention, again showing the various particles, binding members, and types of binding reactions that take place.
Figure 2B:
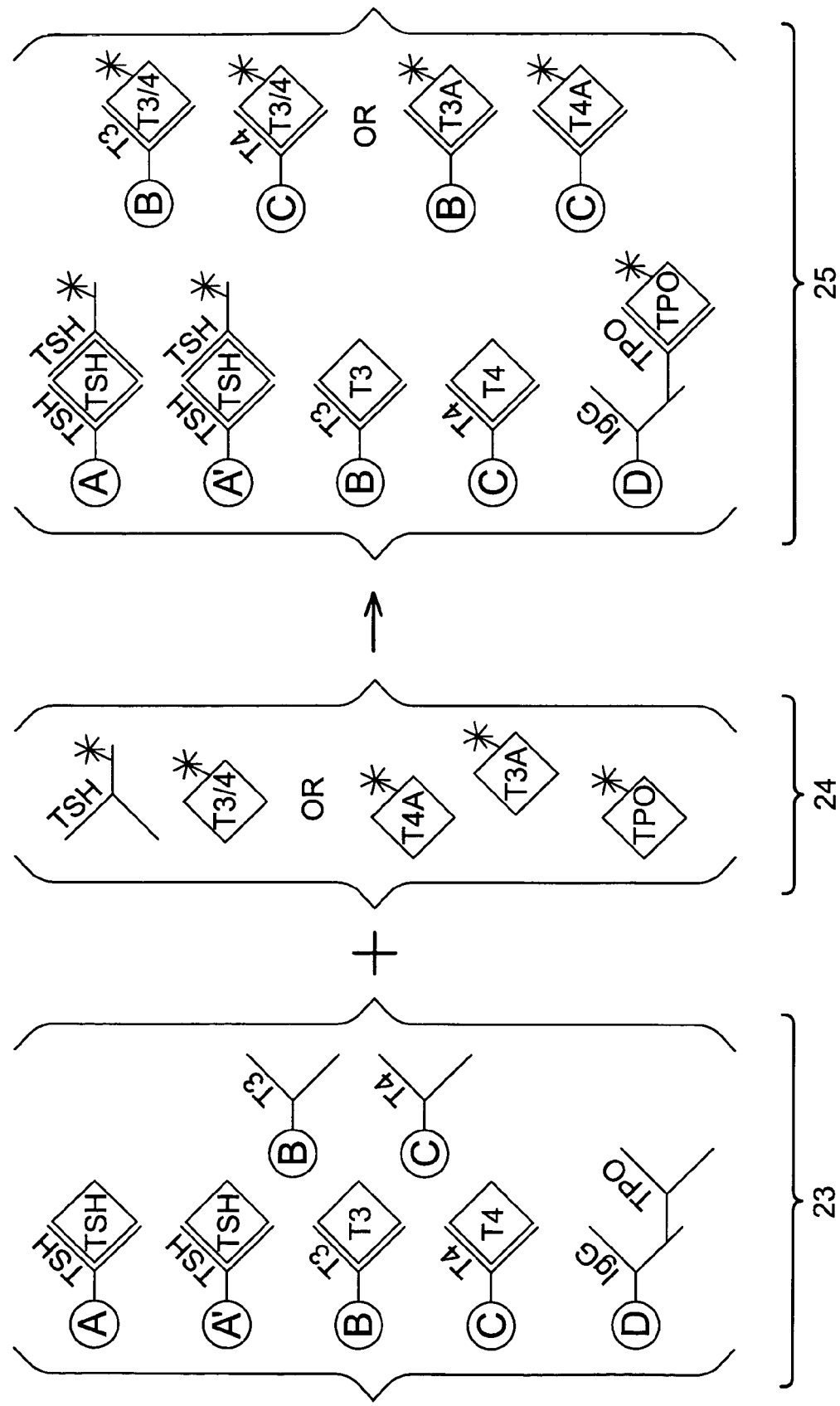
Figure 3:
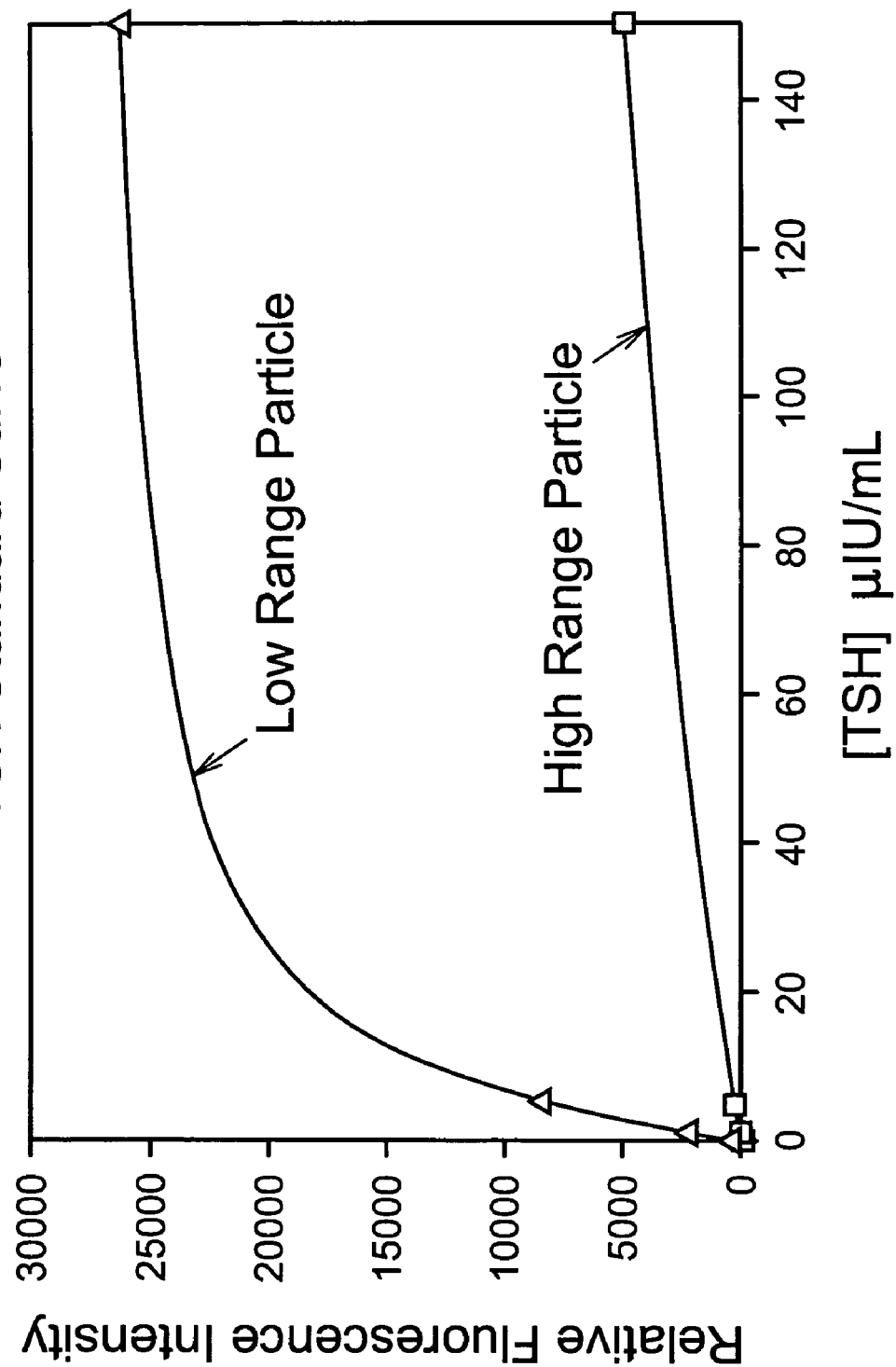
FIG. 3 is a standard curve for TSH generated from a multiplexed assay for TSH, TPO, FT3 and FT4 in accordance with this invention.
Figure 4:
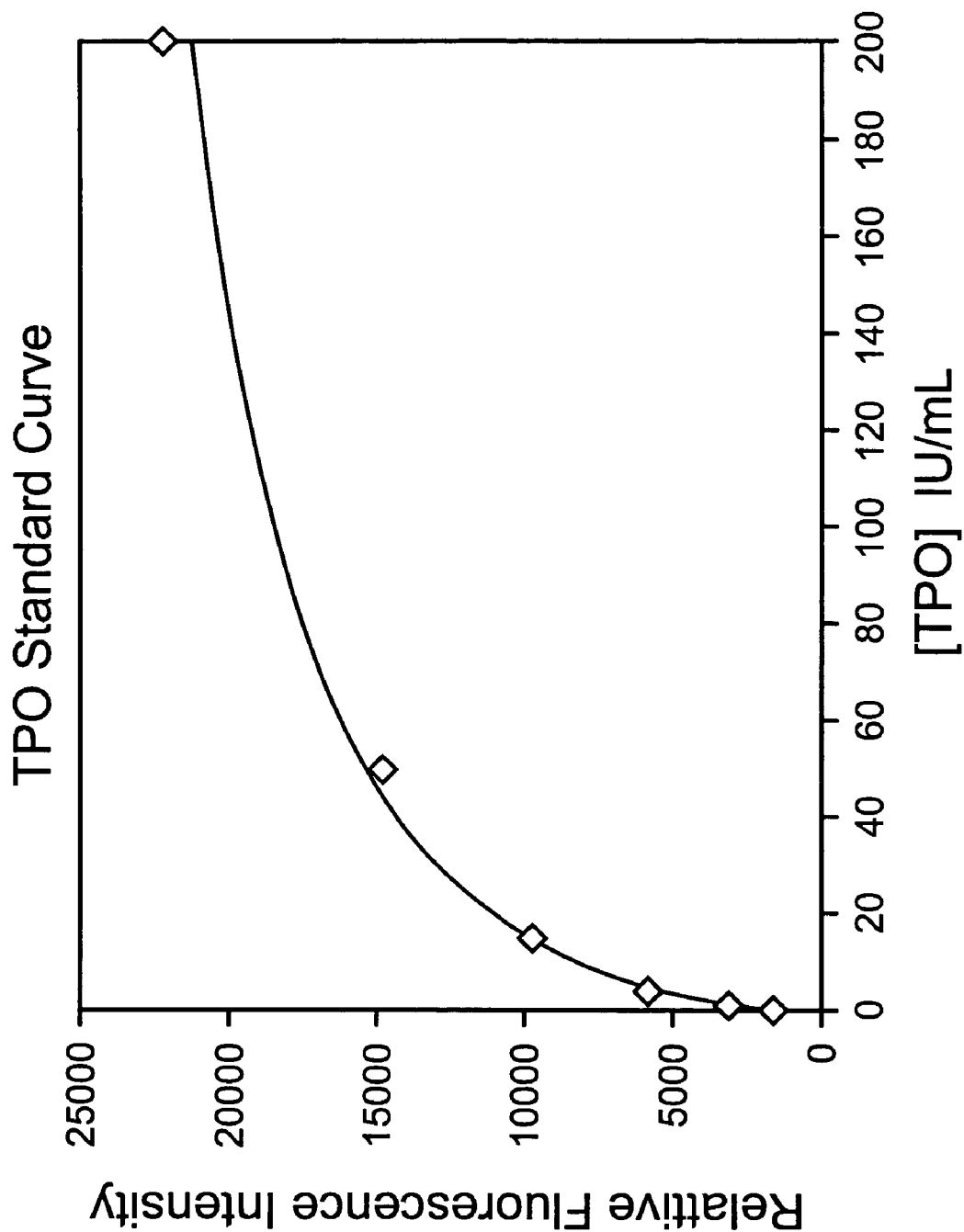
FIG. 4 is a standard curve for TPO generated from a multiplexed assay for TSH, TPO, FT3 and FT4 in accordance with this invention.
Figure 5:
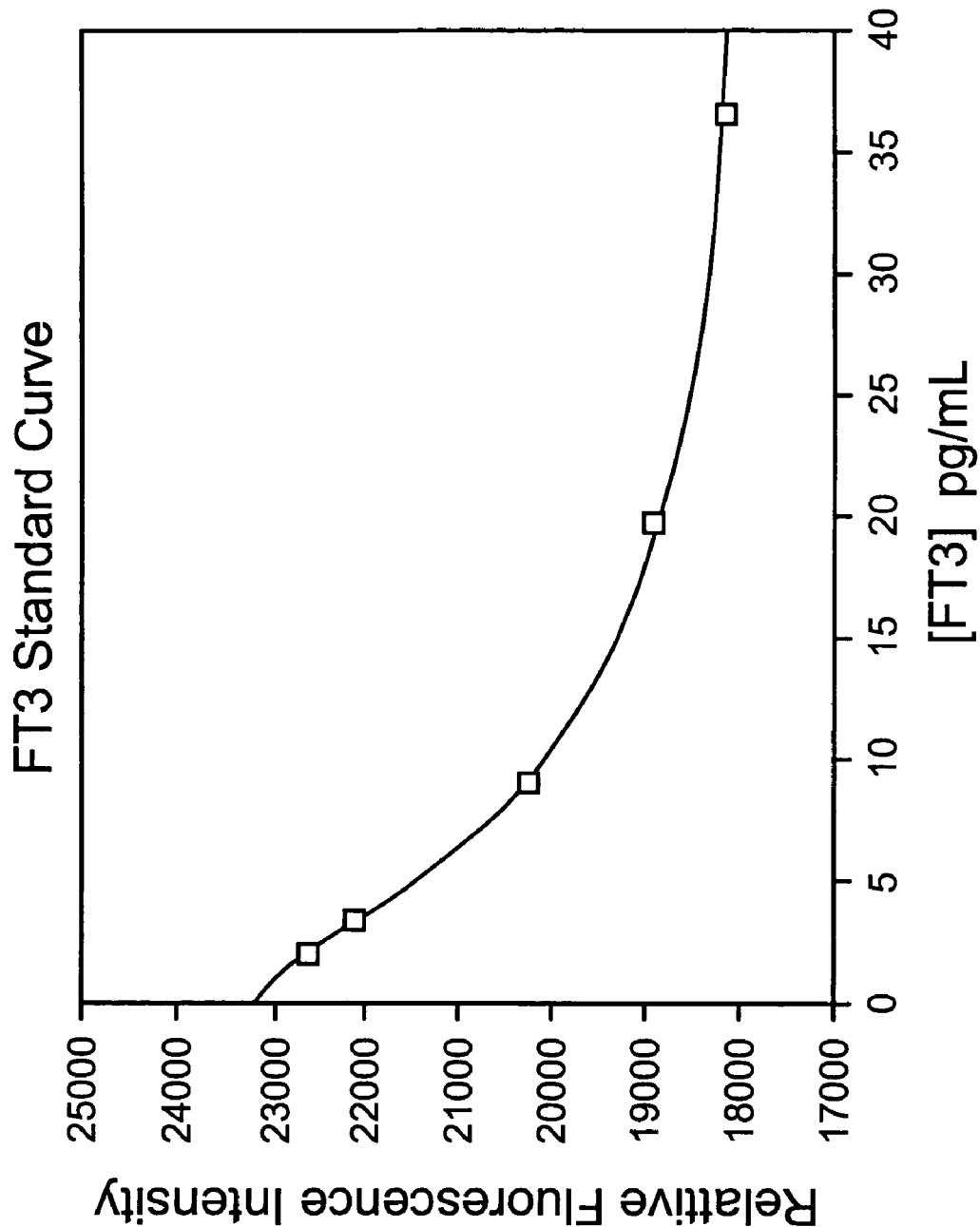
FIG. 5 is a standard curve for FT3 generated from a multiplexed assay for TSH, TPO, FT3 and FT4 in accordance with this invention.
Figure 6:
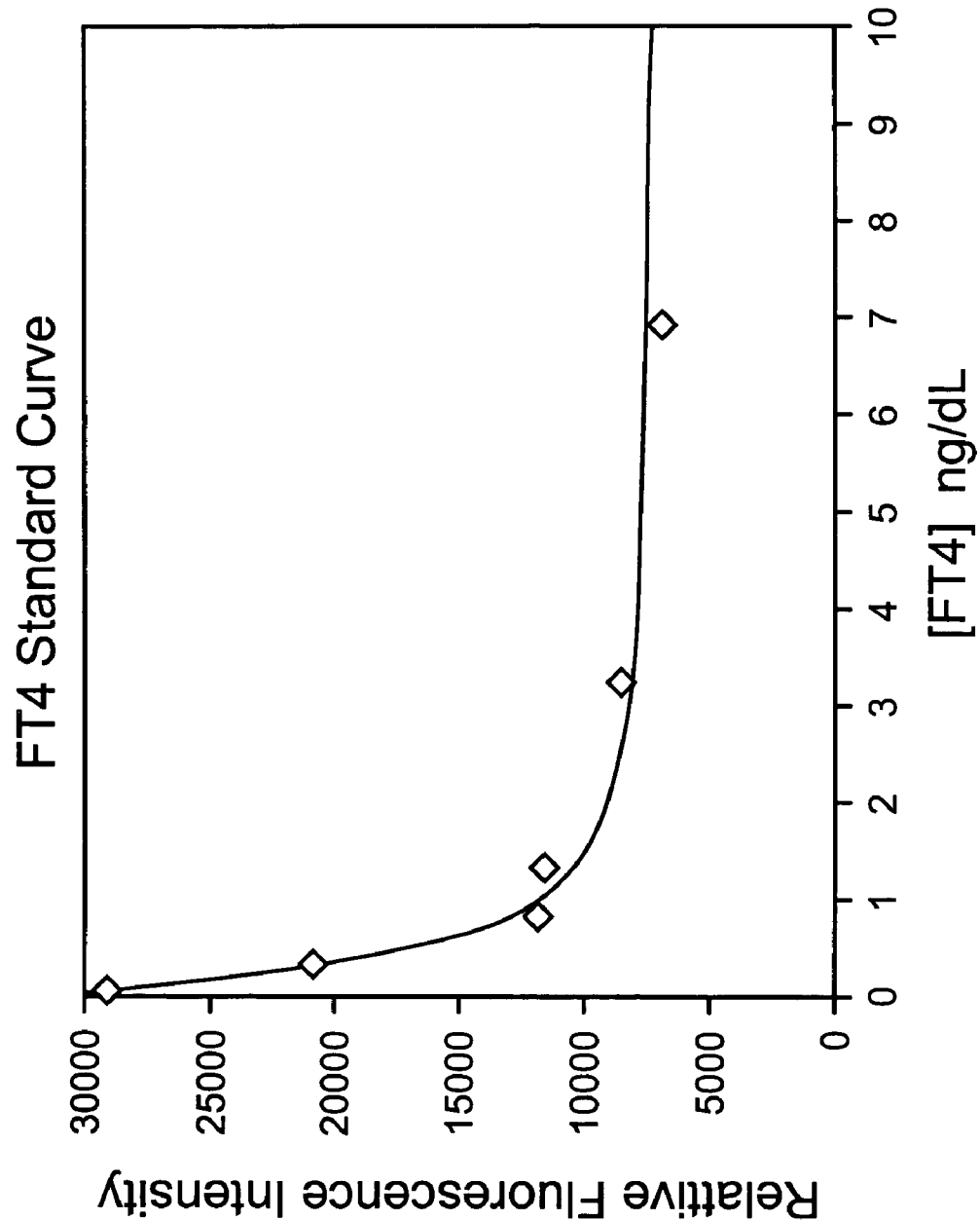
FIG. 6 is a standard curve for FT4 generated from a multiplexed assay for TSH, TPO, FT3 and FT4 in accordance with this invention.

FIGS. 2a and 2b together form a pictorial representation of another assay in accordance with this invention, but one for only four of the marker analytes, TSH, T3, T4, and anti-TPO, and using a direct or "class-capture" serological assay for anti-TPO. The mixture of particles 21 in this assay contains only five distinct groups of particles and is represented by a column of circles with the letters A (and A') through D inside the circles and with either antibodies or antigens attached, using the same types of notations used in FIGS. 1a and 1b. Particles A, A', B, and C are identical to those of FIGS. 1a and 1b. Particle D is coated with anti-human IgG, which will bind all IgG antibodies in the sample. Of the labeled binding members that are added later, however (as described below), the only one that will bind to the IgG antibodies that are thus bound to the D particles is labeled TPO, and thus only those D particles with anti-TPO will be detected. Any D particles to which other IgG antibodies are bound will not take part in the remainder of the assay, and are therefore not shown in the drawing. In preferred embodiments of this assay, no diluting agent is used in the coating of the D particles. The sample 22 to be assayed is shown as containing the four analytes to be detected.

After incubation of the particles and sample, recovery of the particles, and washing, the result is a particle mixture 23 containing the following:

"A", "A'", "B", and "C" particles as in FIGS. 1a and 1b, each having the analyte from the sample bound thereto through the binding member used to form the coating, with additional "B" and "C" particles representing sites on these particles which do not have analyte bound thereto and which will take part in the remainder of the assay.

"D" particles with anti-TPO from the sample bound to the particles through the IgG coating on the particles.

The particle mixture is resuspended with a mixture of labeled binding members 24, differing from the labeled binding members of the assay of FIGS. 1a and 1b by the replacement of the labeled anti-human IgG with labeled TPO. As in FIGS. 1a and 1b, the labels on all of these binding members are represented by asterisks.

After incubation, particle recovery, and washing, the result is a final particle mixture 25 that contains:

"A" and "A'" particles representing the result of sandwich assay, the analyte TSH positioned between the anti-TSH coating on the particle surface and the labeled anti-TSH, the label thus giving a direct indication of the amount of TSH in the sample.

A mixture of "B" particles, labeled and unlabeled, that is the result of a sequential competitive assay, the labeled "B" particles (the two alternatives are shown, depending on which labeled analog was used) representing those sites to which the analyte T3 did not become bound, thereby giving an inverse indication of the amount of T3 in the sample.

A mixture of "C" particles, labeled and unlabeled, that is the result of a sequential competitive assay, the labeled "C" particles (the two alternatives are shown, depending on which labeled analog was used) representing those sites to which the analyte T4 did not become bound, thereby giving an inverse indication of the amount of T4 in the sample.

"D" particles representing the result of a direct or "class-capture" serological assay, the analyte anti-TPO positioned between the anti-IgG coating on the particle surface and the labeled TPO, the label thus giving a direct indication of the amount of anti-TPO in the sample.

Since the markers anti-TPO and anti-Tg are present in high concentrations in the typical serum sample while TSH is present in a relatively low concentration, the assay benefits from the use of a diluting agent as a co-coating material for the particles used in the anti-TPO and anti-Tg assays. The diluting agent is so termed because it competes for the sites available for binding and therefore lowers the coating density of the TPO and Tg on the particles. This reduces the signal from the assays performed on these particles without any substantial loss in the precision of the assay. The diluting agent is thus an agent that does not engage in specific binding with any of the analytes in the sample or with the other assay reagents. Thus, any substance capable of being applied to the particles as a coating that is inert toward the analytes and the labeled binding members used in the assay can be used as the diluting agent. Examples are bovine serum albumin, hydrolyzed porcine gelatin, keyhole limpet hemocyanin, amine-derivatized dextran, and polyacrylic acid. Bovine serum albumin is a preferred example. The amount of diluting agent to be used can vary. Any amount that competes with the TPO and Tg for the binding sites on the particle surface and that will produce an assay that can be replicated with acceptable accuracy can be used.

To reduce the anti-TPO signal to a level that will differentiate high positive from low positive while still being able to attain sufficient assay sensitivity (i.e., being able to differentiate between negative and low positive), the TPO coating density on the group (iv) particles is preferably within the range of from about $0.3$ ng/cm$^2$ to about $0.1$ µg/cm$^2$, and most preferably within the range of from about $0.5$ ng/cm$^2$ to about $50$ ng/cm$^2$. In assays that include anti-Tg, the same range of coating densities may be used.

A further means of improving the assay is to increase the sensitivity of the TSH assay. This can be achieved by the addition of polyethylene glycol (PEG) to the suspension in which the final binding reaction is performed. The labeled binding members and the particles recovered after incubation of the initial assay reagents with the sample are thus suspended in a buffer solution that contains PEG as an additive. This will increase the signal from the TSH assay by increasing the reaction rate due to the presence of the PEG. The molecular weight of PEG used are not critical to the invention, provided that the PEG is fully dissolved in the reaction mixture. Optimal molecular weights and proportions may vary depending on other parameters of the assay mixture and procedure. In most cases, however, the PEG molecular weight will range from about 2,000 to about 20,000, preferably from about 5,000 to about 10,000 (and more preferably approximately 8,000), and the quantity will range from about 0.5% to about 4.0% by weight of the buffer solution, and preferably from about 2.0% by weight to about 3.0% by weight.

The quantity of PEG may also vary, but for most effective results a quantity is chosen that will provide the maximum benefit to the sensitivity of the TSH assay while causing a minimal increase in non-specific binding. The optimal quantity can be determined by varying the weight percentage in the conjugate diluent in increments from 0 to 5%, performing a TSH assay with each, and observing the level of non-specific binding as a function of the PEG level. One should then select the highest PEG level that is accompanied by little or no increase in non-specific binding.

The inclusion of PEG is also useful in embodiments of the invention in which only TSH and T4 are being detected. Preferred types and amounts of PEG for these assays are the same as those described above.

In certain embodiments of the invention, flexibility in the TSH detection to accommodate a large dynamic range is achieved by using two distinguishable subgroups of particles for the TSH group, one for measuring high concentrations of TSH and the other for low concentrations. It has been discovered that large particles provide higher sensitivity than relatively small particles, and that the same is true for particles with a higher coating concentration (regardless of any size difference). Thus, to enable the measurement of both low concentrations and high concentrations of TSH, the two subgroups of particles may differ in particle size, coating density or both. In a particularly preferred embodiment, one subgroup will contain particles that are both of a larger size and a higher antibody coating concentration than the particles of the other subgroup. The former subgroup will then be particularly useful for measuring relatively low concentrations of TSH while the latter will be particularly useful for measuring relatively high concentrations. The two subgroups in combination will thus increase the dynamic range of the assay.

The buffer solutions may also contain proteins that stabilize the assay reagents. An example of a suitable protein is bovine gamma globulin in a buffered saline solution at approximately physiological pH.

The labeled binding members include a composition that has immunological binding affinity toward both anti-T3 and anti-T4 but less than T3 or T4 themselves so that the composition does not displace T3 or T4 that have already become bound to the antibodies. The composition will thus be a structural analog of both T3 and T4 or separate structural analogs of each. Examples of structural analogs of T3 and T4 that can be used are as follows:

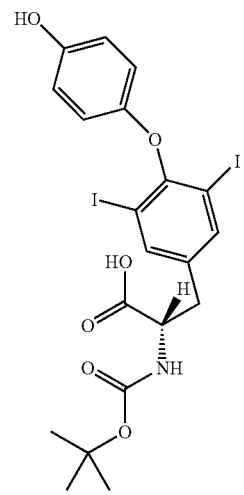

N-tert-butyloxycarbonyl-3,5-diiodo-L-thyronine

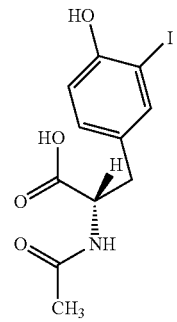

N-acetyl-3-iodo-L-tyrosine

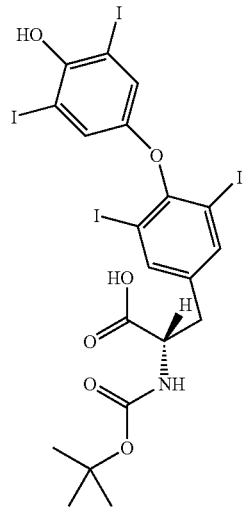

N-tert-butyloxycarbonyl-L-thyroxine

-continued

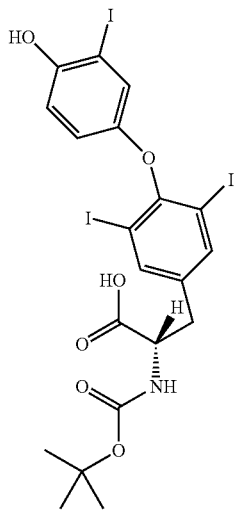

N-tert-butyloxycarbonyl-3',3,5-triiodo-L-thyronine

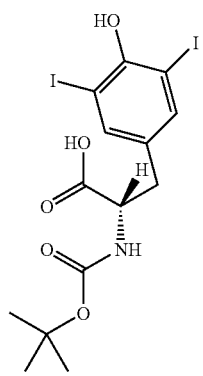

N-tert-butyloxycarbonyl-3,5-diiodo-L-tyrosine

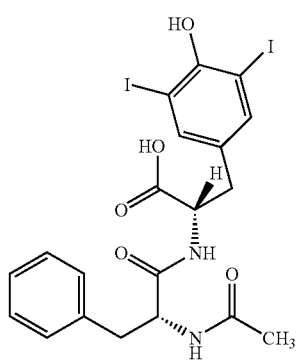

N-acetylphenylalanyl-3,5-diiodo-L-tyrosine

-continued

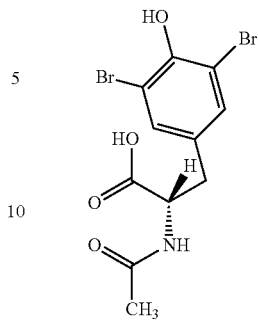

N-acetyl-3,5-dibromo-L-tyrosine

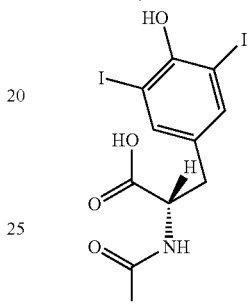

N-acetyl-3,5-diiodo-L-tyrosine

The particles used in the practice of this invention are preferably microscopic in size and formed of a polymeric material. Polymers that will be useful as microparticles are those that are chemically inert relative to the components of the biological sample and to the assay reagents other than the binding member coatings that are affixed to the microparticle surface. Suitable microparticle materials will also have minimal autofluorescence, will be solid and insoluble in the sample and in any buffers, solvents, carriers, diluents, or suspending agents used in the assay, and will be capable of affixing to the appropriate coating material, preferably through covalent bonding. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. The size range of the microparticles can vary and particular size ranges are not critical to the invention. In most cases, the microparticles will range in diameter from about 0.3 micrometers to about 100 micrometers, and preferably from about 0.5 micrometers to about 40 micrometers.

To facilitate the particle recovery and washing steps of the assay, the particles preferably contain a magnetically responsive material, i.e., any material that responds to a magnetic field. Separation of the solid and liquid phases, either after incubation or after a washing step, is then achieved by imposing a magnetic field on the reaction vessel in which the suspension is incubated, causing the particles to adhere to the wall of the vessel and thereby permitting the liquid to be removed by decantation or aspiration. Magnetically responsive materials of interest in this invention include paramagnetic materials, ferromagnetic materials, ferrimagnetic materials, and metamagnetic materials. Paramagnetic materials are preferred. Examples are iron, nickel, and cobalt, as well as metal oxides such as $Fe_3O_4$, $BaFe_{12}O_{19}$, CoO, NiO, $Mn_2O_3$, $Cr_2O_3$, and CoMnP.

The magnetically responsive material can be dispersed throughout the polymer, applied as a coating on the polymer surface or as one of two or more coatings on the surface, or incorporated or affixed in any other manner that secures the material in to the particle. The quantity of magnetically responsive material in the particle is not critical and can vary over a wide range. The quantity can affect the density of the microparticle, however, and both the quantity and the particle size can affect the ease of maintaining the microparticle in suspension for purposes of achieving maximal contact between the liquid and solid phase and for facilitating flow cytometry. An excessive quantity of magnetically responsive material in the microparticles may produce autofluorescence at a level high enough to interfere with the assay results. It is therefore preferred that the concentration of magnetically responsive material be low enough to minimize any autofluorescence emanating from the material. With these considerations in mind, the magnetically responsive material in a particle in accordance with this invention preferably ranges from about 0.05% to about 75% by weight of the particle as a whole. A more preferred weight percent range is from about 1% to about 50%, a still more preferred weight percent range is from about 2% to about 25%, and an even more preferred weight percent range is from about 2% to about 8%.

Coating of the particle surface with the appropriate assay reagent can be achieved by electrostatic attraction, specific affinity interaction, hydrophobic interaction, or covalent bonding. Covalent bonding is preferred. The polymer can be derivatized with functional groups for covalent attachment of the assay reagent by conventional means, notably by the use of monomers that contain the functional groups, such monomers serving either as the sole monomer or as a co-monomer. Examples of suitable functional groups are amine groups (—$NH_2$), ammonium groups (—$NH_3^+$ or —$NR_3^+$), hydroxyl groups (—OH), carboxylic acid groups (—COOH), and isocyanate groups (—NCO). Useful monomers for introducing carboxylic acid groups into polyolefins, for example, are acrylic acid and methacrylic acid.

Linking groups can be used as a means of increasing the density of reactive groups on the particle surface and decreasing steric hindrance. This will increase the range and sensitivity of the assay. Linking groups can also be used as a means of adding specific types of reactive groups to the solid phase surface if needed to secure the particular coating materials of this invention. Examples of suitable useful linking groups are polylysine, polyaspartic acid, polyglutamic acid and polyarginine.

In general, care should be taken to avoid the use of particles that exhibit high autofluorescence. Particles formed by conventional emulsion polymerization techniques from a wide variety of starting monomers are generally suitable since they exhibit at most a low level of autofluorescence. Conversely, particles that have been modified to increase their porosity and hence their surface area, i.e., those particles that are referred to in the literature as "macroporous" particles, are less desirable since they tend to exhibit high autofluorescence. A further consideration is that autofluorescence increases with increasing size and increasing percentage of divinylbenzene monomer.

Multiplexing with the use of microparticles in accordance with this invention is achieved by assigning the microparticles to four, five, six, or more groups, depending on whether the assay is directed to four thyroid disorder markers, five thyroid disorder markers, or the markers plus other components such as interferents. Each group of particles has a distinctive differentiation parameter, which renders that group distinguishable from the other groups by flow cytometry.

One example of a differentiation parameter is the particle diameter, the various groups being defined by nonoverlapping diameter subranges. The widths of the diameter subranges and the spacing between mean diameters of adjacent subranges are selected to permit differentiation of the subranges by flow cytometry, and will be readily apparent to those skilled in the use of and instrumentation for flow cytometry. In this specification, the term "mean diameter" refers to a number average diameter. In most cases, a preferred subrange width is about ±5% CV or less of the mean diameter, where "CV" stands for "coefficient of variation" and is defined as the standard deviation of the particle diameter divided by the mean particle diameter times 100 percent. The minimum spacing between mean diameters among the various subranges can vary depending on the microparticle size distribution, the ease of segregating microparticles by size for purposes of attaching different assay reagents, and the type and sensitivity of the flow cytometry equipment. In most cases, best results will be achieved when the mean diameters of different subranges are spaced apart by at least about 6% of the mean diameter of one of the subranges, preferably at least about 8% of the mean diameter of one of the subranges and most preferably at least about 10% of the mean diameter of one of the subranges. Another preferred subrange width relation is that in which the standard deviation of the particle diameters within each subrange is less than one third of the separation of the mean diameters of adjacent subranges.

Another example of a differentiation parameter that can be used to distinguish among the various groups of particles is fluorescence. Differentiation is accomplished by incorporating various fluorescent materials in the particles, the various fluorescent materials having different fluorescent emission spectra and being distinguishable on this basis.

Fluorescence can in fact be used both as a means of distinguishing the groups from each other and as a means of detection for the assay performed on the particle. The use of fluorescent materials with different emission spectra can serve as a means of distinguishing the groups from each other and also as a means of distinguishing the group classification from the assay detections. An example of a fluorescent substance that can be used as a means of distinguishing groups is fluorescein and an example of a substance that can be used for the assay detection is phycoerythrin. In the use of this example, different particle groups can be dyed with differing concentrations of fluorescein to distinguish them from each other, while phycoerythrin is used as the label on the various labeled binding members used in the assay.

Still other examples of a differentiation parameter that can be used to distinguish among the various groups of particles are light scatter, light emission, or combinations of light scatter and emission. Side angle light scatter varies with particle size, granularity, absorbance and surface roughness, while forward angle light scatter is mainly affected by size and refractive index. Thus, varying any of these qualities can serve as a means of distinguishing the various groups. Light emission can be varied by incorporating fluorescent materials in the microparticles and using fluorescent materials that have different fluorescence intensities or that emit fluorescence at different wavelengths, or by varying the amount of fluorescent material incorporated. By using fluorescence emissions at various different wavelengths, the wavelength difference can be used to distinguish the particle groups from each other, while also distinguishing the labels in the labeled binding members from the labels that differentiate one particle group from another.

In a variation of the above, the microparticles will have two or more fluorochromes incorporated within them so that each microparticle in the array will have at least three differentiation parameters associated with it, i.e., side scatter together with fluorescent emissions at two separate wavelengths. For example, the microparticle can be made to contain a red fluorochrome such as Cy5 together with an orange fluorochrome such as Cy5.5. Additional fluorochromes can be used to further expand the system. Each microparticle can thus contain a plurality of fluorescent dyes at varying wavelengths.

Still another example of a differentiation parameter that can be used to distinguish among the various groups of particles is absorbance. When light is applied to microparticles the absorbance of the light by the particles is indicated mostly by the strength of the laterally (side-angle) scattered light while the strength of the forward-scattered light is relatively unaffected. Consequently, the difference in absorbance between various colored dyes associated with the microparticles is determined by observing differences in the strength of the laterally scattered light.

A still further example of a differentiation parameter that can be used to distinguish among the various groups of particles is the number of particles in each group. The number of particles of each group is varied in a known way, and the count of particles having various assay responses is determined. The various responses are associated with a particular assay by the number of particles having each response.

As the above examples illustrate, a wide array of parameters or characteristics can be used as differentiation parameters to distinguish the microparticles of one group from those of another. The differentiation parameters may arise from particle size, from particle composition, from particle physical characteristics that affect light scattering, from excitable fluorescent dyes or colored dyes that impart different emission spectra and/or scattering characteristics to the microparticles, or from different concentrations of one or more fluorescent dyes. When the distinguishable microparticle parameter is a fluorescent dye or color, it can be coated on the surface of the microparticle, embedded in the microparticle, or bound to the molecules of the microparticle material. Thus, fluorescent microparticles can be manufactured by combining the polymer material with the fluorescent dye, or by impregnating the microparticle with the dye. Microparticles with dyes already incorporated and thereby suitable for use in the present invention are commercially available, from suppliers such as Spherotech, Inc. (Libertyville, Ill., USA) and Molecular Probes, Inc. (Eugene, Oreg., USA).

The labels used in the labeled binding members may be any label that is capable of emitting detectable signal. Preferred such labels are fluorophores. As noted above, fluorophores may also be incorporated into the particles themselves are also a means of distinguishing one group of particles from another. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

The following is a list of examples of fluorophores:
4-acetamido-4'-isothiocyanatostilbene-2,2'disulfonic acid
acridine
acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin
7-amino-4-methylcoumarin (AMC, Coumarin 120)
7-amino-4-trifluoromethylcoumarin (Coumaran 151)
cyanine dyes
cyanosine
4',6-diaminidino-2-phenylindole (DAPI)
5',5"-dibromopyrogallol-sulfonaphthalein (Bromopyrogallol Red)
7-diethylamino-3-(4'-isothiocyanatophenyl)-4-methylcoumarin diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin
eosin isothiocyanate
erythrosin B
erythrosin isothiocyanate
ethidium
5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene
pyrene butyrate
succinimidyl 1-pyrene butyrate
quantum dots
Reactive Red 4 (Cibacron™ Brilliant Red 3B-A)
6-carboxy-X-rhodamine (ROX)
6-carboxyrhodamine (R6G)
lissamine rhodamine B sulfonyl chloride rhodamine (Rhod)
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)

tetramethyl rhodamine
tetramethyl rhodamine isothiocyanate (TRITC)
riboflavin
rosolic acid
lanthanide chelate derivatives The fluorophores (or other labels) can be used in combination, with a distinct label for each analyte. Preferably, however, a single label is used for all labeled binding members, the assays being differentiated solely by the differentiation parameter distinguishing the individual particle groups from each other.

The attachment of any of these fluorophores to the binding members described above to form assay reagents for use in the practice of this invention is achieved by conventional covalent bonding, using appropriate functional groups on the fluorophores and on the binding members. The recognition of such groups and the reactions to form the linkages will be readily apparent to those skilled in the art.

Methods of and instrumentation for flow cytometry are known in the art, and those that are known can be used in the practice of the present invention. Flow cytometry in general resides in the passage of a suspension of the microparticles as a stream past a light beam and electro-optical sensors, in such a manner that only one particle at a time passes the region of the sensors. As each particle passes this region, the light beam is perturbed by the presence of the particle, and the resulting scattered and fluoresced light are detected. The optical signals are used by the instrumentation to identify the subgroup to which each particle belongs, along with the presence and amount of label, so that individual assay results are achieved. Descriptions of instrumentation and methods for flow cytometry are found in the literature. Examples are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Md., USA: Williams and Williams, 1993), pp. 535-544; Lindmo et al., "Immunometric Assay Using Mixtures of Two Particle Types of Different Affinity," *J. Immunol. Meth.* 126: 183-189 (1990); McHugh, "Flow Cytometry and the Application of Microsphere-Based Fluorescence Immunoassays,"*Immunochemica* 5: 116 (1991); Horan et al., "Fluid Phase Particle Fluorescence Analysis: Rheumatoid Factor Specificity Evaluated by Laser Flow Cytophotometry," *Immunoassays in the Clinical Laboratory*, 185-189 (Liss 1979); Wilson et al., "A New Microsphere-Based Immunofluorescence Assay Using Flow Cytometry," *J. Immunol. Meth.* 107: 225-230 (1988); Fulwyler et al., "Flow Microsphere Immunoassay for the Quantitative and Simultaneous Detection of Multiple Soluble Analytes," *Meth. Cell Biol.* 33: 613-629 (1990); Coulter Electronics Inc., United Kingdom Patent No. 1,561,042 (published Feb. 13, 1980); and Steinkamp et al., *Review of Scientific Instruments* 44(9): 1301-1310 (1973).

Similarly, methods of and instrumentation for applying and removing a magnetic field as part of an automated assay are known to those skilled in the art and reported in the literature. Examples of literature reports are Forrest et al., U.S. Pat. No. 4,141,687 (Technicon Instruments Corporation, Feb. 27, 1979); Ithakissios, U.S. Pat. No. 4,115,534 (Minnesota Mining and Manufacturing Company, Sep. 19, 1978); Vlieger, A. M., et al., Analytical Biochemistry 205:1-7 (1992); Dudley, Journal of Clinical Immunoassay 14:77-82 (1991); and Smart, Journal of Clinical Immunoassay 15:246-251 (1992). All of the citations in this and the preceding paragraph are incorporated herein by reference.

The samples that can be analyzed in accordance with this invention include any biological samples that may contain the markers that are sought to be quantified. Examples are serum, blood eluates, plasma, cerebrospinal fluid, urine, and cell extracts. The samples may be human samples, including those from adult patients as well as children and infants, or they may be samples from mammals in general, including domesticated dogs and other pets as well as livestock, and zoo animals.

EXAMPLES

The following examples are offered for purposes of illustration and are intended neither to limit nor to define the invention in any manner. The buffer solutions used in these examples were as follows:

| | |
|---|---|
| Wash Buffer: | 50 mM phosphate buffer pH 7.4, 150 mM sodium chloride, 0.1% sodium azide and 0.1% tween 20. |
| FT4 Particle Coating Buffer: | 50 mM phosphate buffer pH 7.4, 150 mM sodium chloride, 0.1% sodium azide, 0.1% tween 20 and 0.5% bovine gamma-globulin |
| Particle Diluent: | 50 mM phosphate buffer pH 7.4, 150 mM sodium chloride, 0.1% sodium azide and 0.25% bovine gamma globulin. |
| Storage Buffer: | 50 mM phosphate buffer, pH 7.4, 150 mM sodium chloride, 0.1% sodium azide, 0.1% Tween 20 and 1% bovine serum albumin. |
| Conjugate Diluent: | 50 mM phosphate buffer pH 7.4, 150 mM sodium chloride, 0.1% sodium azide, 2.75% polyethylene glycol 8000 and 0.25% bovine gamma-globulin |

The particles and other materials used in the examples were prepared as follows:

Coating of Particles with Anti-TSH Using 12-μm Particles:

Into a microfuge tube were placed 4.23 mg of 12 μm dyed magnetic particles. The particles were then washed 3 times by: adding 1 mL of 25 mM 2-(N-morpholino)-ethanesulfonic acid (MES) pH 6.2, centrifuging and pipeting off the supernatant. To the pellet were added: 388 μL deionized water, 160 μL 0.5M MES buffer, 184 μL of 94.33 mg/mL N-hydroxysulfosuccinimide (NHSS) in deionized water and 200 μL of 50 mg/mL 1-ethyl-3-(3 -dimethylaminopropyl)carbodiimide hydrochloride (EDC) in deionized water to the pellet. The tube was agitated for 30 minutes, then centrifuged, and the supernatant was pipetted off and discarded. The particles were then washed 2 times by: adding 1 mL of 25 mM MES pH 6.2, centrifuging and pipeting off the supernatant. To the pellet was added the following: 129.8 μL deionized water, 25 μL of 0.5M MES and 70.2 μL of anti-TSH antibody (386 μg, 5.5 mg/mL). The tube was agitated for 4 hours, followed by the addition of 100 μL of a 250 mM ethanolamine solution in 25 mM MES pH 6.2. The tube for then agitated for 30 minutes, followed by the addition of 750 μL of storage buffer, then centrifuged, and the supernatant pipetted off and discarded. The particles were then washed 5 times by: adding 1 mL of storage buffer, centrifuging and pipeting off the supernatant. Storage buffer (1 mL) was then added and the particles and buffer were kept at 4° C.

Coating of Particles with Anti-TSH Using 8-μm Particles:

Into a microfuge tube was placed 2.82 mg of 8 μm dyed magnetic particles. The particles were washed 3 times by: adding 1 mL of 25 mM 2-(N-morpholino)-ethanesulfonic acid (MES) pH 6.2, centrifuging and pipeting off the supernatant. To the pellet were added: 388 μL deionized water, 160 μL 0.5M MES buffer, 184 μL of 94.33 mg/mL N-hydroxysulfosuccinimide (NHSS) in deionized water and 200 µL of 50 mg/mL 1-ethyl-3-(3-dimethylaminopropyl)carbodiimide hydrochloride (EDC) in deionized water. The tube was agitated for 30 minutes, then centrifuged, and the supernatant pipetted off and discarded. The particles were then washed 2 times by: adding 1 mL of 25 mM MES pH 6.2, centrifuging and pipetting off the supernatant. To the pellet were added the following: 25 µL of 0.5M MES and 225 µL of solution of 0.257 mg/mL anti-TSH antibody and 1.716 mg/mL bovine serum albumin. The tube was agitated for 4 hours, then 100 µL of a 250 mM ethanolamine solution in 25 mM MES pH 6.2 were added. The tube was then agitated for 30 minutes, and 750 µL of storage buffer was added. The tube was centrifuged, pipetted off and discarded. The particles were washed 5 times by: adding 1 mL of storage buffer, centrifuging and pipetting off the supernatant. Storage buffer (1 mL) was then added and the particles and buffer were kept at 4° C.

Coating of Particles with TPO:

Into a microfuge tube were placed 2.82 mg of 8 µm dyed magnetic particles. The particles were washed 3 times by: adding 1 mL of 25 mM 2-(N-morpholino)-ethanesulfonic acid (MES) pH 6.2, centrifuging and pipeting off the supernatant. To the pellet were added: 388 µL deionized water, 160 µL 0.5M MES buffer, 184 µL of 94.33 mg/mL N-hydroxysulfosuccinimide (NHSS) in deionized water and 200 µL of 50 mg/mL 1-ethyl-3-(3-dimethylaminopropyl)carbodiimide hydrochloride (EDC) in deionized water to the pellet. The tube was then agitated for 30 minutes protected from light, then centrifuged, and the supernatant pipetted off and discarded. The particles were then washed 2 times by: adding 1 mL of 25 mM MES pH 6.2, centrifuging and pipeting off the supernatant. To the pellet were added the following: 25 µL of 0.5M MES and 225 µL of solution of 1.72 µg/mL TPO and 1.716 mg/mL bovine serum albumin. The tube was then agitated for 4 hours protected from light. After this time, a 250 mM ethanolamine solution (100 µL) in 25 mM MES pH 6.2 was added, and the tube was agitated for 30 minutes protected from light. Storage buffer (750 µL) was added, and the supernatant was centrifuged, pipetted off and discarded. The particles were then washed 5 times by: adding 1 mL of storage buffer, centrifuging and pipetting off the supernatant. Storage buffer (1 mL) was then added and the particles ad buffer were kept at 4° C.

Coating of Particles with Anti-FT4:

Into a microfuge tube were placed 5.64 mg of 8 µm dyed magnetic particles. The particles were washed 3 times by: adding 1 mL of 25 mM 2-(N-morpholino)-ethanesulfonic acid (MES) pH 6.2, centrifuging and pipeting off the supernatant. To the pellet were added: 388 µL deionized water, 160 µL 0.5M MES buffer, 184 µL of 94.33 mg/mL N-hydroxysulfosuccinimide (NHSS) in deionized water and 200 µL of 50 mg/mL 1-ethyl-3-(3-dimethylaminopropyl)carbodiimide hydrochloride (EDC) in deionized water to the pellet. The tube was agitated for 30 minutes protected from light, then centrifuge, and the supernatant pipetted off and discarded. The particles were then washed 2 times by: adding 1 mL of 25 mM MES pH 6.2, centrifuging and pipeting off the supernatant. To the pellet was added the following: 25 µL of 0.5M, 28.3 µL of 2.73 mg/mL anti-T4 antibody and 196.7 µL deionized water. The tube was agitated for 4 hours protected from light, and then a 250 mM ethanolamine solution in 25 mM MES pH 6.2 (100 µL) was added. The tube was agitated for 30 minutes protected from light, and 750 µL of FT4 particle coating buffer was added. The tube was centrifuged, and the supernatant pipetted off and discarded. The tube was then washed 5 times by: adding 1 mL of FT4 particle coating buffer, centrifuging and pipeting off the supernatant. To the tube was then added 1 mL of FT4 particle coating buffer and the tube was kept at 4° C.

Coating of Particles with Anti-FT3:

Into a microfuge tube were placed 5.64 mg of 8 µm dyed magnetic particles. The particles were washed 3 times by: adding 1 mL of 25 mM 2-(N-morpholino)-ethanesulfonic acid (MES) pH 6.2, centrifuging and pipeting off the supernatant. To the pellet was added: 388 µL deionized water, 160 µL 0.5M MES buffer, 184 µL of 94.33 mg/mL N-hydroxysulfosuccinimide (NHSS) in deionized water and 200 µL of 50 mg/mL 1-ethyl-3-(3-dimethylaminopropyl)carbodiimide hydrochloride (EDC) in deionized water. The tube was then agitated for 30 minutes protected from light, then centrifuged, and the supernatant pipeted off and discarded. The tube was then washed 2 times by: adding 1 mL of 25 mM MES pH 6.2, centrifuging and pipeting off the supernatant. To the pellet was added the following: 99 µL of 7.8 mg/mL anti-T3 antibody and 151 µL of 25 mM MES, pH 6.1. The tube was then agitated for 4 hours protected from light, followed by the addition of 100 µL of a 250 mM ethanolamine solution in 25 mM MES pH 6.2. The tube was then agitated for 30 minutes protected from light, followed by the addition of 750 µL of FT4 particle coating buffer. The tube was then centrifuge, and the supernatant pipetted off and discarded. The tube was then washed 5 times by: adding 1 mL of FT4 particle coating buffer, centrifuging and pipeting off the supernatant. FT4 particle coating buffer (1 mL) was then added and the particles and buffer kept at 4° C.

Preparation of Anti-TSH Labeled with Phycoerythrin (Anti-TSH-PE):

Sulfosuccinimidyl 6-[3'-(2-pyridyldithio)-propionamido] hexanoate (sulfo-LC-SPDP) (4.4 mg) was dissolved in 2 mL of 50 mM PBS (2.2 mg/mL). This solution (20 µL) was added to 250 µL of a 4 mg/mL solution of B-phycoerythrin in 50 mM PBS, and the resulting solution was allowed to sit in the dark at ambient temperature for 2.5 hours. Into a microfuge tube was placed 2.58 mg of anti-TSH antibody. Sulfosuccinimidyl 4-[N-maleimidomethyl]-cyclohexane-1-carboxylate (sulfo-SMCC) (4.4 mg) was dissolved in 2 mL of 50 mM PBS. This solution (49.6 µL) was then added immediately to the anti-TSH antibody solution, and the resulting solution was allowed to sit I hour in the dark at ambient temperature. After the incubation time had elapsed, a 77 mg/mL solution (62.1 µL) of dithiothreitol (DTT) in 50 mM PBS was added to the PE+sulfo-LC-SPDP reaction mixture, and the resulting solution was incubated for 30 minutes in the dark at ambient temperature. The PE+sulfo-LC-SPDP+DTT and anti-TSH+ sulfo-SMCC reaction mixtures were separately dialyzed against 4 changes of 1L of 50 mM PBS (30 minutes between changes of dialysis solution, ambient temperature, protected from light). The dialyzed solutions were mixed. The antibody-PE mixture was kept at 4° C. overnight protected from light. The next day a solution of N-ethylmaleimide (2 mg/mL in 50 mM PBS) (10 µL) was added to the antibody-PE mixture, and the resulting mixture was incubated for 1 hour at ambient temperature. After this time the mixture was purified by HPLC using a size-exclusion column (guard column: SEC400 80×7.8 mm, column: SEC400 300×7.8 mm, mobile phase: 50 mM PBS, flow rate: 1 mL/minute). To the combined fractions were added bovine serum albumin (solid) and 10% NaN3 (in deionized water) such that the resulting concentrations were 10 mg/mL and 0.1%, respectively.

Preparation of N-t-Butyloxycarbonyl-3,5-diiodotyrosine-phycoerythrin (DITboc-PE):

A 39 mg/mL solution of N-t-butyloxycarbonyl-3,5-diiodotyrosine N-hydroxysuccinimide ester in dimethylsulfoxide solution (10 µL) was added to a solution of 700µL of 1.43 mg/mL B-phycoerythrin in 50 mM phosphate buffer, pH 7.5. The mixture was gently agitated for 4 hours at ambient temperature protected from light. After this time the mixture was purified by HPLC using a size-exclusion column (guard column: SEC400 80×7.8 mm, column: SEC400 300×7.8 mm, mobile phase: 50 mM PBS, flow rate: 1 mL/minute).

Preparation of N-Acetyloxycarbonyl-3,5-diiodotyrosine-phycoerythrin (MITboc-PE):

A solution was prepared by dissolving 10 mg of N-acetyl-3-iodotyrosine in 167 µL of dimethylformamide (DMF). This solution (97 µL) was added to 6.6 mg of 1-ethyl-3-(3-dimethylaminopropyl)carbodiimide hydrochloride EDC. To this mixture was added 64 µL of 60 mg/mL N-hydroxysuccinimide in DMF. The resulting mixture was placed on a vortexer for 75 minutes at ambient temperature. After this time 97 µL of this reaction mixture was transferred to 1 mL of 12 mg/mL B-phycoerythrin in 50 mM PBS. The product mixture was wrapped in foil and placed on a vortexer overnight at ambient temperature. The next day the product was purified on a G75-120 size exclusion column (1.5×50 cm) using 50 mM PBS as the mobile phase.

Multiplex Assay Procedure for TSH (Using Both High and Low Range Particles), TPO, FT4, and FT3:

1. The anti-TSH-coated particles (both sizes) and the TPO-coated particles are placed in a microfuge tube where they are washed 3 times by: adding 1 mL of particle diluent, centrifuging and pipeting off the supernatant. The anti-T4- and anti-T3-coated particles are then added to the pellet, which is then diluted to approximately 2×10$^5$ particles/mL/region.
2. The sample (100 µL) and the mixture of particles of step 1 (100 µL) are placed in a titertube (Bio-Rad Laboratories, Inc., Hercules, Calif., USA, Catalog No. 223-9390), and all titertubes are placed in a rack.
3. The rack of titertubes is incubated at 37° C. in a heating block for 15 minutes with continuous vortexing to keep the particles suspended. Light is excluded during this period.
4. After incubation, the rack of titertubes is placed in a magnetic separator where the particles are allowed to rest for 3 minutes during which time they are drawn by the magnets to the sides of the titertubes.
5. The supernatant is aspirated.
6. Wash buffer (300 µL) is added to each tube.
7. The particles are allowed 3 minutes to be drawn by the magnets to the sides of the titertubes.
8. The supernatant is aspirated.
9. Steps 6 to 8 are repeated three more times.
10. To the particles are added 50 µL of a mixture of the anti-TSH-PE and DITboc-PE conjugates plus anti-human IgG-PE (this labeled antibody is obtainable from Jackson Immunoresearch Laboratories, West Grove, Pa., USA, Catalog No. 109-106-098,) diluted with conjugate diluent.
11. The rack of titertubes is incubated at 37° C. in a heating block for 15 minutes with light excluded and continuous vortexing to keep the particles suspended.
12. After incubation, the rack of titertubes is placed in a magnetic separator, and allowed 3 minutes for the particles to be drawn by the magnets to the sides of the titertubes.
13. The supernatant is aspirated.
14. Wash buffer (300 µL) is added to each tube.
15. The particles are allowed 3 minutes to be drawn by the magnets to the sides of the titertubes.
16. The supernatant is aspirated.
17. Steps 14 to 16 are repeated once.
18. The particles are suspended in 35 µL of wash buffer.
19. The titertubes are placed in a light-tight box until read by a LX100 instrument (Luminex Corporation, Austin, Tex., USA) in multiplex mode.

Standard curves for TSH, TPO, FT4, and FT3 that were generated using this assay procedure are shown in FIGS. 3, 4, 5, and 6, respectively.

Multiplex Assay Procedure for FT4 and FT3:

1. The anti-T4 and anti-T3 coated particles are placed in a microfuge tube and diluted to approximately 2×10$^5$ particles/mL/region.
2. The sample (100 µL) and 100 µL of the mixture of particles of step 1 are placed in a titertube (Bio-Rad Laboratories, Inc., Catalog No. 223-9390). All titertubes are placed in a rack.
3. The rack of titertubes is incubated at 37° C. in a heating block for 5 minutes with light excluded and continuous vortexing to keep the particles suspended.
4. After incubation, MITboc-PE (50 µL) diluted with particle diluent is added.
5. The rack is returned to the heating block and vortexed continuously for 15 minutes with light excluded.
6. The rack of titertubes is then placed in a magnetic separator and allowed 3 minutes for the particles to be drawn by the magnets to the sides of the titertubes.
7. The supernatant is aspirated.
8. Wash buffer (300 µL) is added to each tube.
9. The particles are allowed 3 minutes to be drawn by the magnets to the sides of the titertubes.
10. The supernatant is aspirated.
11. Steps 8 to 10 are repeated two more times.
12. DITboc-PE diluted with conjugate diluent (50 µL) is then added.
13. The rack of titertubes is incubated at 37° C. in a heating block for 15 minutes with light excluded and continuous vortexing to keep the particles suspended.
14. The rack of titertubes is then placed in a magnetic separator, and allowed 3 minutes for the particles to be drawn by the magnets to the sides of the titertubes.
15. The supernatant is aspirated.
16. Wash buffer (300 µL) is added to each tube.
17. The particles are allowed 3 minutes to be drawn by the magnets to the sides of the titertubes.
18. The supernatant is aspirated.
19. Steps 16 to 18 are repeated two more times.
20. The particles are suspended in 35 µL of wash buffer.
21. The titertubes are read using a LX100 instrument in multiplex mode.

Standard curves for FT3 and FT4 that were generated using this assay procedure are shown in FIGS. 7 and 8, respectively.

The foregoing is offered primarily for purposes of illustration. It will be readily apparent to those skilled in the art that the operating conditions, materials, procedural steps and other parameters described herein may be further modified or substituted in various ways without departing from the spirit and scope of the invention. It will also be apparent that the features of this invention may be adaptable to other analytes and analyte combinations to permit the simultaneous performance of different types of immunological assays on a single sample and in a single reaction mixture.

What is claimed is:

1. A method for analyzing a single patient sample to simultaneously determine levels of thyroid stimulating hormone and thyroxine, said method comprising:
   (a) incubating said sample with a mixture of particles comprising magnetically responsive material in a first suspension, said mixture of particles comprised of groups (i) and (ii):
      (i) particles coated with anti-thyroid stimulating hormone, and
      (ii) particles coated with anti-thyroxine,
      the groups distinguishable from each other by a flow cytometry-distinguishable characteristic that is independent of the coatings of subparagraphs (i) and (ii);
   (b) recovering said particles from said first suspension by subjecting said suspension to a magnetic field to cause said particles to adhere to a reaction vessel wall, and incubating said recovered particles with a mixture of labeled binding members capable of binding to the recovered particles in a second suspension, said mixture of labeled binding members comprising:
      (1) labeled anti-thyroid stimulating hormone, and
      (2) a labeled analog toward which anti-thyroxine has immunological binding affinity, but in which said immunological binding affinity is less than that of anti-thyroxine toward thyroxine; and
   (c) recovering said particles from said second suspension by subjecting said suspension to a magnetic field to cause said particles to adhere to a reaction vessel wall and detecting the amount of label bound to said particles thus recovered while correlating by flow cytometry the amount of label thus detected to the group to which said label is bound, thereby simultaneously obtaining values individually representative of the levels of thyroid stimulating hormone and thyroxine.

2. A method in accordance with claim 1 in which said labeled binding members are binding members labeled with fluorescent labels.

3. A method in accordance with claim 2 in which said fluorescent labels are B-phycoerythrin.

4. A method in accordance with claim 1 in which said labeled binding members are labeled with a common label.

5. A method in accordance with claim 1 in which said particles include dyes, each of groups (i) and (ii) including a distinct dye that is distinguishable by flow cytometry over the dyes of each other group, and step (c) comprises distinguishing such dyes by flow cytometry while detecting the amount of label bound to said particles.

6. A method in accordance with claim 1 in which group (i) is comprised of two subgroups differing from each other by particle size such that one subgroup provides a substantially greater sensitivity for measuring lower concentrations of TSH, than the other.

7. A method according to claim 6 in which one group of particles provides a greater sensitivity for measuring lower concentrations of TSH than the other, and the second subgroup of particles provides a greater sensitivity for measuring higher concentrations of TSH than the other.

8. A method in accordance with claim 1 in which group (i) is comprised of two subgroups differing from each other by coating density of anti-thyroid stimulating hormone such that one subgroup provides a substantially greater sensitivity for measuring lower concentrations of TSH, than the other.

9. A method according to claim 8 in which one group of particles provides a greater sensitivity for measuring lower concentrations of TSH than the other, and the second subgroup of particles provides a greater sensitivity for measuring higher concentrations of TSH than the other.

10. A method in accordance with claim 1 in which group (i) is comprised of two subgroups differing from each other by both particle size and coating density of anti-thyroid stimulating hormone such that one subgroup provides a substantially greater sensitivity for measuring lower concentrations of TSH, than the other.

11. A method according to claim 10 in which one group of particles provides a greater sensitivity for measuring lower concentrations of TSH than the other, and the second subgroup of particles provides a greater sensitivity for measuring higher concentrations of TSH than the other.

* * * * *